US012797361B2

(12) United States Patent
Madhu

(10) Patent No.: US 12,797,361 B2
(45) Date of Patent: Nov. 17, 2026

(54) ADMINISTRATION METHOD OF A CHEMOTHERAPEUTIC AGENT

(71) Applicant: Suchit Madhu, Ahmedabad (IN)

(72) Inventor: Suchit Madhu, Ahmedabad (IN)

( * ) Notice: Subject to any disclaimer, the term of this patent is extended or adjusted under 35 U.S.C. 154(b) by 438 days.

(21) Appl. No.: 18/273,956

(22) PCT Filed: Jan. 31, 2022

(86) PCT No.: PCT/IN2022/050079
§ 371 (c)(1),
(2) Date: Jul. 24, 2023

(87) PCT Pub. No.: WO2022/168113
PCT Pub. Date: Aug. 11, 2022

(65) Prior Publication Data

US 2024/0408051 A1 Dec. 12, 2024

(30) Foreign Application Priority Data

Feb. 2, 2021 (IN) ............................ 202121004469

(51) Int. Cl.
*A61K 31/36* (2006.01)
*A61P 35/00* (2006.01)

(52) U.S. Cl.
CPC .............. *A61K 31/36* (2013.01); *A61P 35/00* (2018.01)

(58) Field of Classification Search
None
See application file for complete search history.

(56) References Cited

FOREIGN PATENT DOCUMENTS

| | | | | |
|---|---|---|---|---|
| EP | 2942629 A1 * | 11/2015 | ....... G01N 33/57426 |
| WO | WO 2016/200835 A1 | 12/2016 | |
| WO | WO 2017/095751 A1 | 6/2017 | |
| WO | WO 2019/232161 A1 | 12/2019 | |
| WO | WO-2019232479 A2 * | 12/2019 | ....... G01N 33/57426 |

OTHER PUBLICATIONS

Daniel Hirschhorn-Cymerman et al., “OX40 engagement and chemotherapy combination provides potent antitumor immunity with concomitant regulatory T cell apoptosis”, May 9, 2009, pp. 1103-1116.

International Search Report dated May 5, 2022, issued by the U.S. Patent Office, in corresponding application PCT/IN2022/050079.

* cited by examiner

*Primary Examiner* — Noble E Jarrell
(74) *Attorney, Agent, or Firm* — Kevin J Fournier Intellectual Property Legal Services Ltd.; Kevin J Fournier

(57) ABSTRACT

The present invention provides an administration method of a chemotherapeutic agent preferably Stiripentol for the treatment of solid and blood cancer. The present chemotherapeutic agent is target specific and substantially reduces the growth of the cancer cells. The target specific administration of the said Stiripentol inhibits the production of lactate dehydrogenase, to reduce the growth of the cancer cells. Further the present chemotherapeutic agent substantially reduces the cell viability, and the proliferation activity of the cancer cells.

8 Claims, 4 Drawing Sheets

ADMINISTRATION METHOD OF A CHEMOTHERAPEUTIC AGENT

CROSS-REFERENCE TO RELATED APPLICATIONS

This application is a national stage of International Application No. PCT/IN2022/050079, filed Jan. 31, 2022, which claims the benefit of Indian Application No. 202121004469, filed Feb. 2, 2021, in the Indian Patent Office, the disclosures of which are incorporated herein by reference.

FIELD OF INVENTION

The present invention generally relates anticancer activity of Stiripentol and the method of administrating a drug. More particularly it relates to administration of a chemotherapeutic agent for treatment of solid and blood cancer brain tumor that substantially reduces or inhibits the growth of the cancer cells.

BACKGROUND OF INVENTION

Every year more than 17 million people gets cancer and >9 million number of people dies because of it. The biggest challenge in cancer treatment is to target cancer cells and not affecting normal cells. Chemotherapeutic agents are non-specific in nature and targets rapidly dividing cells. Due to that chemotherapeutic agents produce various side effects. Moreover, cancer resistance is one big hurdle to treat cancer. Resistance is when initially effective drugs are not effective anymore. Due to these there is dire need for new agents to treat cancer to save lives. Cancer cells show Warburg effect where they are highly glycolytic in nature, They also secrete high amount of lactic acid in their microenvironment. Inhibiting this phenomenon can be great strategy to treat cancer.

Stiripentol is anti-epileptic approved to treat Dravet syndrome. Exact mechanism of action of this drug not known. Recently, it has shown to inhibit LDH enzyme. There is no effect determined against cancer ever reported by stiripentol.

Due to BBB it is hard to develop anticancer agent targeting Brian. Major challenge in treating any brain cancer is delivering drug to brain due to blood Brain Barrier (BBB). BBB is a physical and metabolic barrier between the brain and the systematic circulation, which serves to regulate and protect the microenvironment of the brain. It is composed of a monolayer of brain capillary endothelial cells. The restriction of brain uptake by the BBB arises by the presence of tight junctions (zonulae occludens) between adjacent endothelial cells and a relative paucity of fenestrae and pinocytotic vesicles within endothelium of cerebral arterioles, capillaries, and venules. The brain capillary endothelial cells are surrounded by an ECM, pericytes, and astrocyte foot processes. Because of the presence of the BBB, it is hard for circulating molecules to gain access into brain. Due to that, number of drugs targeting brain cancer is limited.

At present, Timozolamide is used as first line therapy for patients suffering from brain cancer. It acts as alkylating agent prodrug, delivering a methyl group to purine bases of DNA (O6-guanine; N7-guanine and N3-adenine). Due to its alkylating nature, it causes many side effects in patients.

Therefore, there is a need of chemotherapeutic agent that can treat brain tumor. Due to side effects of chemotherapeutic agents and drug resistance, there is necessity to have better drugs to treat solid and blood cancer.

Prior Art and its Disadvantages

U.S. patent application Ser. No. 10/350,192B2, relates to a lactate dehydrogenase inhibitor and an antiepileptic drug containing isosafrole (or a derivative thereof) as an active ingredient. Stiripentol is an antiepileptic drug. Stiripentol was first developed as a brain disease drug, and it was then shown to be effective for Dravet syndrome (one of childhood epilepsies) which is one of refractory epilepsies. Stiripentol is now clinically used as a drug for Dravet syndrome in Europe (approved in 2007) and Japan (approved in 2012) under the trade name of Diacomit. However, although Stiripentol therapy was successful in Dravet syndrome, it has not been successful at present in clinical trials for other epilepsies (especially adult epilepsies).

However, the cited patent application only describes the development of Stiripentol and similar class of drug as an antiepileptic agent other than Dravet syndrome by causing metabolic inhibition. It fails to mention the impact of Stiripentol drug on solid or blood tumor.

Another patent application no. WO2017140658A1 relates to the use of stiripentol and their derivatives for decreasing urinary oxalate concentration in an individual. Stiripentol or 4,4-dimethyl-1-[3,4-(methylendioxy)-phenyl]-1penten-3-ol, is already proposed as an antiepileptic indicated in severe myoclonic epilepsy in infancy. Among its main effects, Stiripentol inhibits the uptake of gamma-aminobutyric acid (GABA) and is also an inhibitor of several cytochrome P450 isoenzymes, especially CYP1A2 and CYP3A4. Stiripentol is also known for its use in the prevention or the treatment of peripheral neuropathy. It describes method of reducing oxalate concentration in urine by Stiripentol and similar class of drugs. The method provides protection from diseases and/or conditions like hyperoxaluria, urolithiasis, nephrocalcinosis and some renal failures kidney stone by reducing oxalate concentration in urine. The method of treatment can be achieved by inhibition of LDH-5 enzyme, which is responsible for oxidation reaction of glyoxylate to oxylate.

However, the cited patent only provides the method of reducing urinary oxalate concentration in urine by Stiripentol and similar class of drugs. It fails to provide the solution for treatment of brain cancer.

Disadvantages of Prior Art

- Most or all of the cited prior arts fail to provide the administration of chemotherapeutic agent to treat the solid or blood tumor.
- Most or all of the prior art fails to provide administration of Stiripentol that is a target specific drug.
- Most or all of the cited prior art fails to provide administration of Stiripentol that is target specific and inhibits tumor metastasis.
- Most or all of the cited prior arts fail to provide administration of Stiripentol that substantially reduces the growth of cancer cells using glycolysis (and LDH enzyme-shall we use that as other patent describes it as LDH inhibitor) as their primary energy source.
- Most or all of the cited prior art documents fails to provide administration of Stiripentol that reduces the rate of the glycolysis and LDH enzyme and thus reduces the lactate production.
- Most or all of the cited prior art fails to decrease the proliferation activity of the cancer cells.

Objects of Invention

The primary object of the present invention is to provide administration of chemotherapeutic agent for treating solid and blood tumor.

Another object of the present invention is to provide administration of chemotherapeutic agent that uses Stiripentol drug as chemotherapeutic agent for the treatment of solid and blood cancer.

Yet another object of the present invention is to provide administration of Stiripentol that significantly modulates metabolic nature of cancer cells and immune cells in tumor microenvironment.

Yet another object of the present invention is to provide administration of Stiripentol that is a target specific drug.

Yet another object of the present invention is to provide administration of Stiripentol that reduces the growth of cancer cells by inhibiting LDH enzyme and reducing glycolytic activity using glycolysis.

Yet another object of the present invention is to provide administration of Stiripentol that reduces lactate production and thus reduce glycolysis.

Yet another object of the present invention is to obviate the disadvantages of the prior art.

DETAILED DESCRIPTION OF INVENTION

Figure 1:
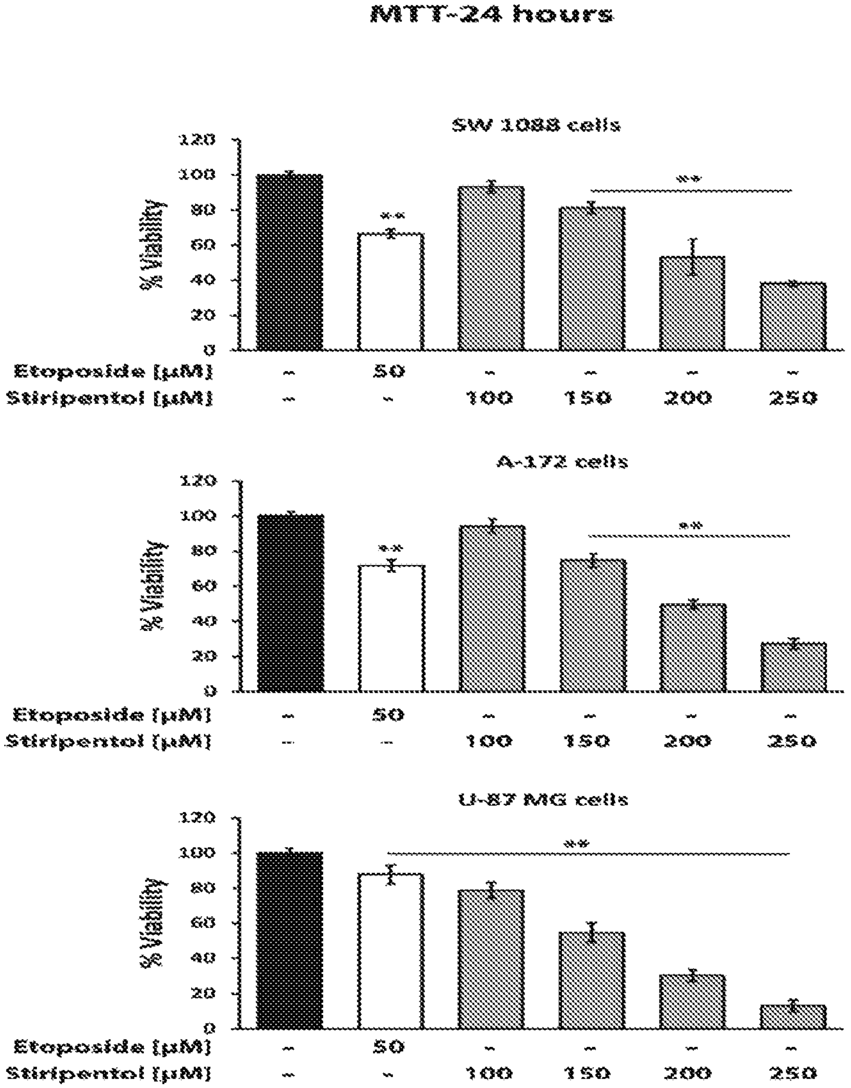
FIG. 1 Shows the cell viability using MTT dye on various cells lines

Embodiments of the present disclosure present technological improvements as solution to one or more of the above-mentioned technical problems recognized by the inventor in conventional practices and existing state of the art.

The accompanying drawings constitute a part of this specification and illustrate one or more embodiments of the invention. Preferred embodiments of the invention are described in the following with reference to the drawings, which are for the purpose of illustrating the present preferred embodiments of the invention and not for the purpose of limiting the same. For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale.

The following detailed description illustrates embodiments of the present disclosure and ways in which the disclosed embodiments can be implemented. Although some modes of carrying out the present disclosure have been disclosed, those skilled in the art would recognize that other embodiments for carrying out or practicing the present disclosure are also possible.

Referring to FIG. 1 to 4, the present disclosure seeks to provide an administration method of a chemotherapeutic agent to treat and reduce the cancer effects in the patient. Said chemotherapeutic agent used in the present invention is Stiripentol. The present Stiripentol is a target specific drug that reduces the growth of the harmful cancer cells. Wherein the target specific administration of the present Stiripentol inhibits the production of lactate dehydrogenase to reduce the growth of the cancer cells.

According to an embodiment the present chemotherapeutic agent used is preferably Stiripentol (4,4-dimethyl-1-[3,4-(methylendioxy)-phenyl]-1penten-3-ol). Said Stiripentol is an antiepileptic drug, that is used to treat the seizure disorder.

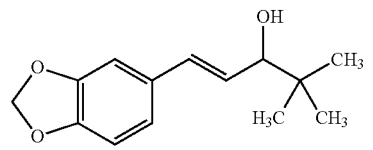

Stiripentol

Said Stiripentol, substantially inhibits the action of lactate dehydrogenase that reduces glycolysis by cancer cells produce adenosine triphosphate (ATP). Thus the rate of glycolysis in the cancer cells decreases substantially resulting in inhibition of tumor metastasis. Further the inhibition uptake of Lactate dehydrogenase by the cancer cells ensures glycolysis in the leukocytes. Thus the growth of the cancer cells reduces substantially.

In an embodiment the present invention provides a method for administrating the chemotherapeutic drug, wherein said method comprises following steps:

Potentiating the action of chemotherapeutic drug by inhibiting angiogenesis and by modulating level of extracellular lactate.

Immunomodulation of immune cells to act against cancer cells, inhibit to promote cancer and reduce inhibitory of extracellular lactate on immune cells.

Immunomodulation of immune cells by inhibiting LDH enzyme activity in immune cells relying on glycolysis as source of energy during activation.

According to another embodiment the present invention utilizes BrdU assay, 3.7% formaldehyde solution, Triton X-100, spectrophotometer, MTT dye (3-(4,5-dimethylthiazol-2-yl)-2,5-diphenyltetrazolium bromide) and neutral red dye (3-amino-7-dimethylamino-2-methyl-phenazine hydrochloride), formazan crystals, isolated LDH enzyme from U-87 MG, Confluent plates.

According to an embodiment various possible examples of the present invention are disclosed herein under.

Example 1

The present disclosure uses Stiripentol as a chemotherapeutic agent to treat brain tumor. Referring to FIG. 1, the cell viability is determined by using MTT dye (3-(4,5-dimethylthiazol-2-yl)-2,5-diphenyltetrazolium bromide and neutral red dye (3-amino-7-dimethylamino-2-methyl-phenazine hydrochloride). Cancer cells from various cell lines (SW 1088 cells, A-172 cells, U-87 MG cells) are incubated with, Stiripentol in the concentration range of 100-250 μ/M. Simultaneously all the cell lines are incubated with etoposide (positive control) in the concentration of 50 μ/M. The cells lines were thereafter treated with 0.05% (w/v) MTT dye for 4 h at 37° C. and DMSO. The cells lines that received no treatment are used as negative control. The results shows there is substantial decrease in the cell viability of the cancer cell that are treated with Stiripentol at concentration 250 μ/M.

According to an embodiment the Cell viability can be determined using MTT dye (3-(4,5-dimethylthiazol-2-yl)-2,5-diphenyltetrazolium bromide) and neutral red dye (3-amino-7-dimethylamino-2-methyl-phenazine hydrochloride). Cells can be incubated with drugs at indicated concentrations and time points. For the MTT assay, at the end of the drug treatments, cells are treated with 0.05% (w/v) MTT dye for 4 h at 37° C. The formazan crystals are dissolved in DMSO and absorbance was measured at 570 nm using the spectrophotometer. Similarly for neutral red assay, Cells are incubated with drugs at indicated concentrations and time points. Briefly, at the end of the drug treatments, cells are incubated with 40 μg/ml neutral red dye for 4 h at 37° C. Cells were then destained using a solution (50% ethanol, 49% deionized water, and 1% glacial acetic acid). Absorbance was measured at 540 nm using Tecan spectrophotometer.

Example 2

Figure 2:
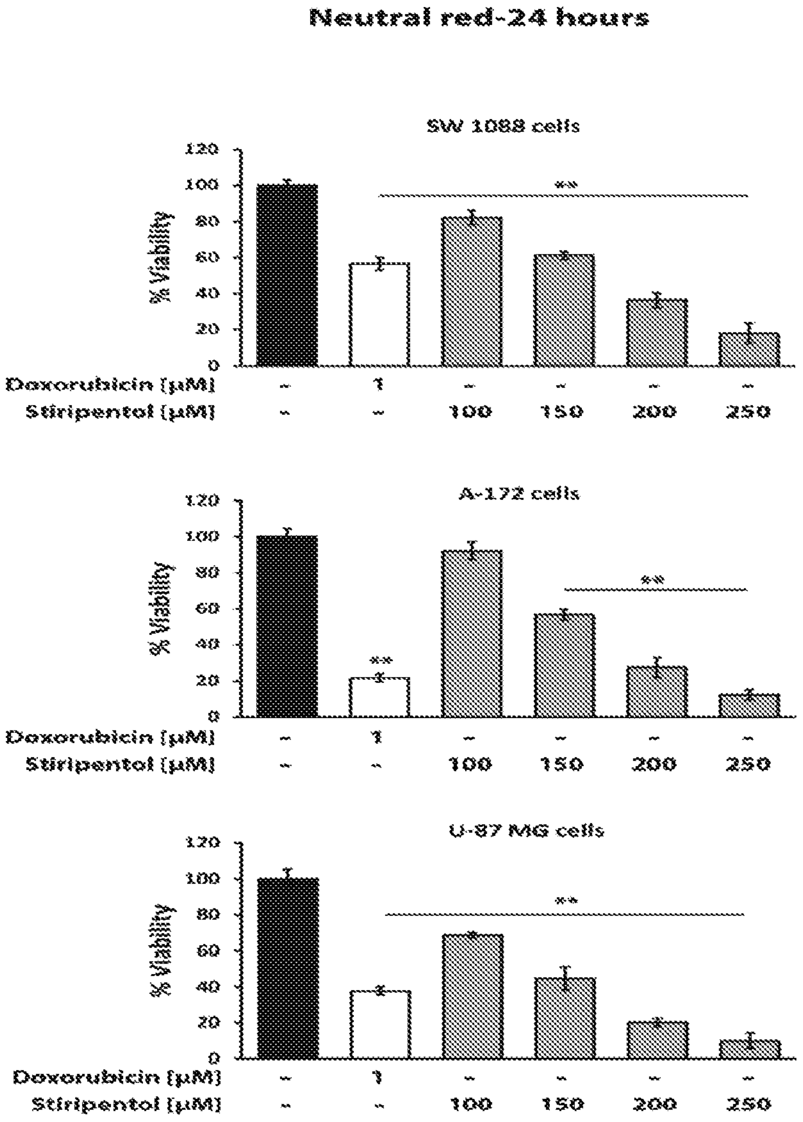
FIG. 2 Shows the cell viability using natural red dye on various cells lines FIG. 3 Shows the cell proliferation activity using BrdU dye on various cell lines FIG. 4 Shows the LDH inhibitory activity of Stiripentol on U-87 MG cells

Referring to FIG. 2, cell viability can be determined by utilizing natural red dye (3-amino-7-dimethylamino-2-methyl-phenazine hydrochloride). Cancer cells from various cell lines namely SW 1088 cells, A-172 cells, U-87 MG cells are incubated with Stiripentol and Doxorubicin (used as positive control) in the concentration range of 50-250 μ/M. thereafter the cells are treated with 40 μg/ml neutral red dye for 4 h at 37° C. and destained. Untreated cancer cells are used as negative control. The results obtained after 24 hours shows there is substantial reduction in the viability of the cancer cells line that are treated with Stiripentol in the concentration of 250 μ/M.

Example 3

Figure 3:
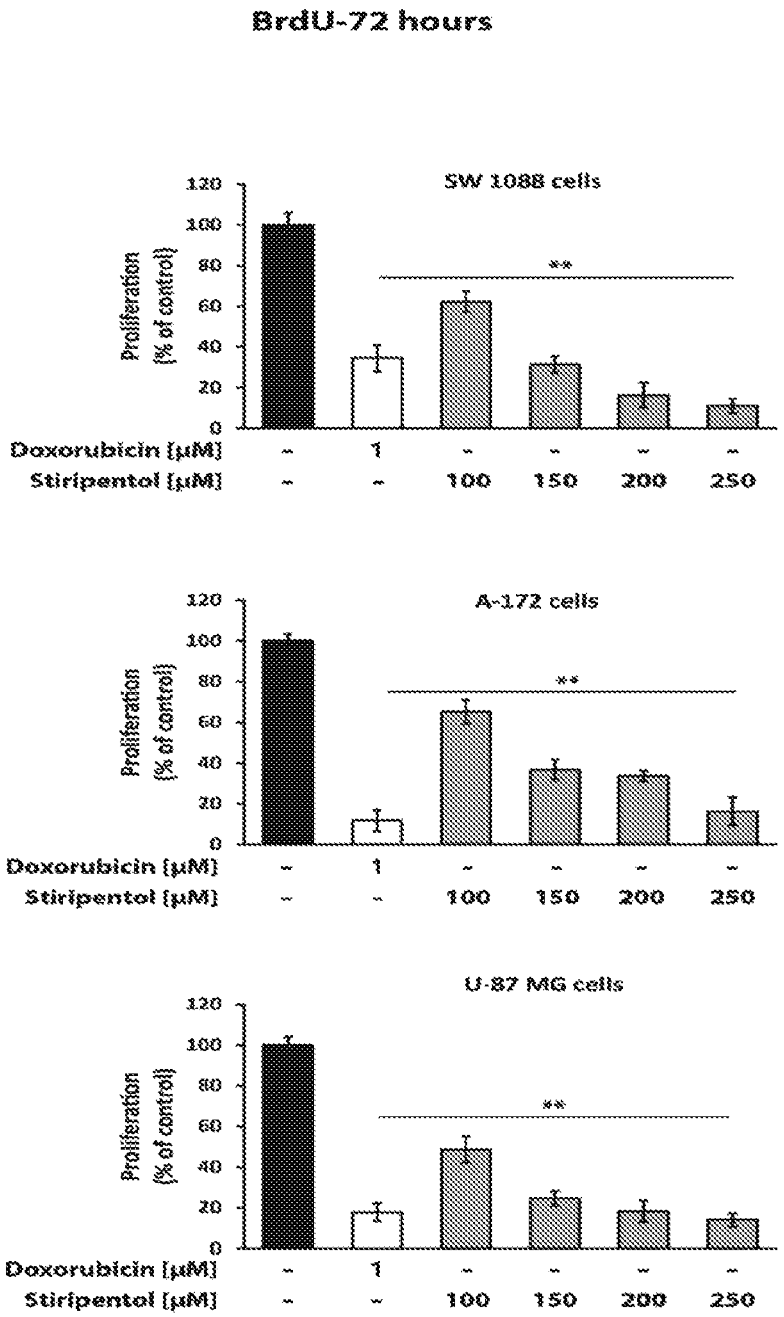

Referring to FIG. 3, cell proliferative activity of the cancer cells can be determined using BrdU assay. Cancer cells from cell lines namely SW 1088 cells, A-172 cells, U-87 MG cells are incubated with Stiripentol and Doxorubicin (used as positive control) in the concentration range of 50-250 μ/M. The cell lines are treated with 10 micromolar of BrdU for 2 hours and washed with PBS and Formaldehyde. The treated cell lines are incubated with primary antibody and the secondary antibody. The untreated cells lines are used as negative control here. The results are obtained after 72 hours that show there is substantial reduction in the cell proliferation activity of the cell lines that are treated with Stiripentol at 250 μ/M.

Example 4

Figure 4:
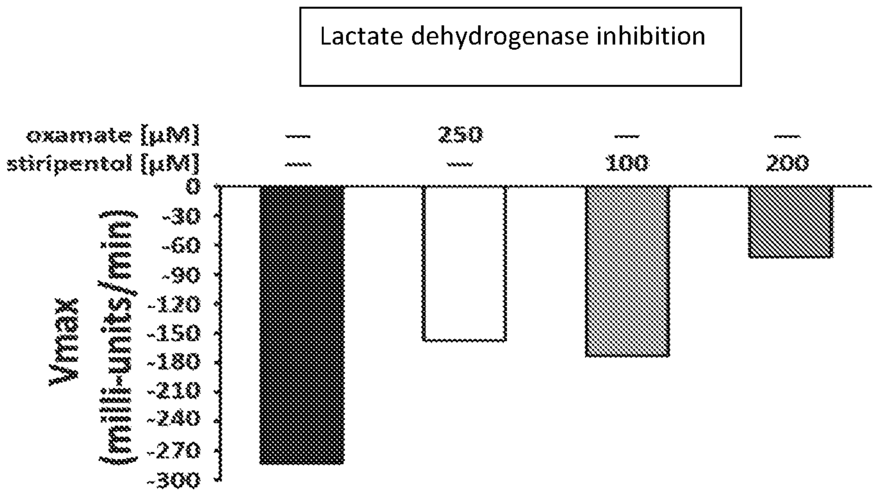

Cancer cells up regulate glycolysis to support rapid growth. LDH is an enzyme part of glycolysis. Referring to FIG. 4 LDH inhibitory activity of Stiripentol can be measured by using LDH enzyme from U-87 MG. The cell culture media is treated with HEPES buffer. Cells are homogenized and treated with the respective drug. Cancer cells thereafter are incubated with Oxamate (used as positive control) at 250 μ/M and Stiripentol at 100 and 200 μ/M respectively. The treated cells are mixed with 1.7 mM of pyruvate and 250 μM of β-NADH. LDH enzyme production in the cells is observed after 24 hours that shows there is substantial decrease in the production of LDH enzyme in the cells that are incubated with Stiripentol at 200 μ/M.

ADVANTAGES OF INVENTION

- The present invention provide administration of Stiripentol for treating and/or preventing solid and blood tumor.
- The use of stiripentol drug as an anticancer agent to treat various forms of malignancies of solid and blood.
- The administration of Stiripentol reduces lactate production that inhibits tumor metastasis and helps immune system to act effectively against cancer cells and inhibit immune cells to support tumor growth.
- The Stiripentol significantly modulates metabolic nature of cancer cells and immune cells in tumor microenvironment.
- Said Stiripentol is a target specific drug.
- The administration of Stiripentol reduces the rate of the glycolysis and thus reduces the lactate production.
- Administration of Stiripentol inhibits the glycolysis in the cancer cells and ensures glycolysis in the healthy cells.
- The administration of Stiripentol substantially reduces the cell viability of the cancer cells
- The administration of Stiripentol substantially decreases the cell proliferation activity of the cancer cells

The invention claimed is:

1. A method of reducing or inhibiting growth of cancer cells in a subject in need thereof, wherein said method comprises:

administering to the subject one or more chemotherapeutic drugs;

wherein the one or more chemotherapeutic drugs inhibits lactate dehydrogenase enzyme in immune cells or the cancer cells of the subject;

wherein the cancer cells are from a solid tumor or blood cancer, and wherein the one or more chemotherapeutic drugs comprises stiripentol or its salt.

2. The method of claim 1, wherein the cancer cells are from a solid tumor.

3. The method of claim 1, wherein the cancer cells are from a blood cancer.

4. The method of claim 1, wherein the cancer cells are malignant glioma cancer cells.

5. The method of claim 1, wherein the cancer cells are glioblastoma cancer cells.

6. The method of claim 1, wherein the cancer cells are astrocytoma cancer cells.

7. The method of claim 1, wherein the cancer is a brain cancer.

8. The method of claim 1, wherein the one or more chemotherapeutic drugs is stiripentol.

* * * * *